United States Patent [19]

Zöllner

[11] 4,050,015
[45] Sept. 20, 1977

[54] CONTROL OF MICROWAVE GENERATOR-CAVITY RESONATOR COMBINATIONS FOR GAS ANALYZER

[75] Inventor: Wolf-Dieter Zöllner, Aachen, Germany

[73] Assignee: Hartmann & Braun Aktiengesellschaft, Frankfurt am Main, Germany

[21] Appl. No.: 702,844

[22] Filed: July 6, 1976

[30] Foreign Application Priority Data

July 4, 1975 Germany .............................. 2529829

[51] Int. Cl.² ........................................... G01R 27/04
[52] U.S. Cl. ............................................... 324/58.5 C
[58] Field of Search ..................... 324/58.5 C, 58.5 B, 324/58 C

[56] References Cited

U.S. PATENT DOCUMENTS

| 2,580,968 | 1/1952 | Sproull ....................... 324/58.5 C X |
| 2,792,548 | 5/1957 | Hershberger .................... 324/58.5 C |
| 2,849,613 | 8/1958 | Dicke ............... 324/58.5 C |
| 3,437,922 | 4/1969 | Miller, Jr. ........................ 324/58.5 C |

Primary Examiner—Stanley T. Krawczewicz
Attorney, Agent, or Firm—Ralf H. Siegemund

[57] ABSTRACT

A frequency spectrum with center frequency and lower, discrete side bands is derived from a microwave generator and fed to a cavity resonator of the reflector type so that a reflected component can be coupled out varying at an amplitude which represents the deviation of the spectrum center frequency from the cavity resonance frequency. The variable signal is used to control the microwave frequency generation. An invariable component, also coupled out, is indicative of the concentration of a gas having an absorption line at the resonance frequency.

9 Claims, 9 Drawing Figures

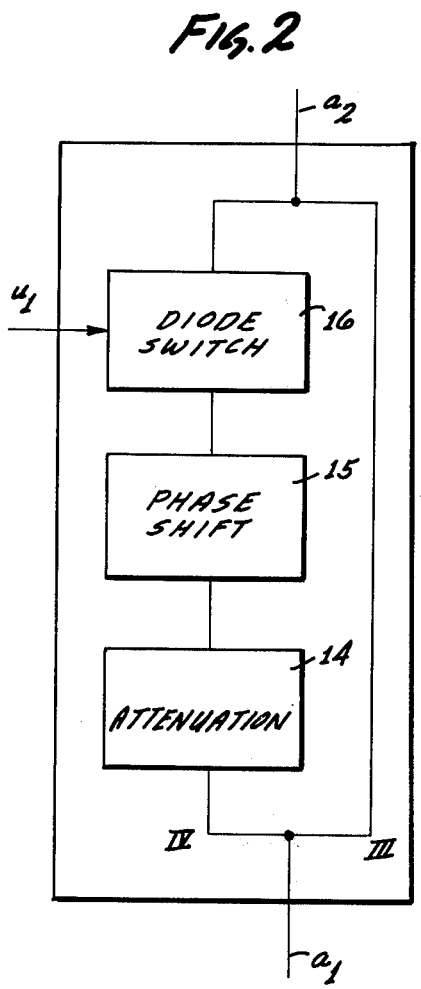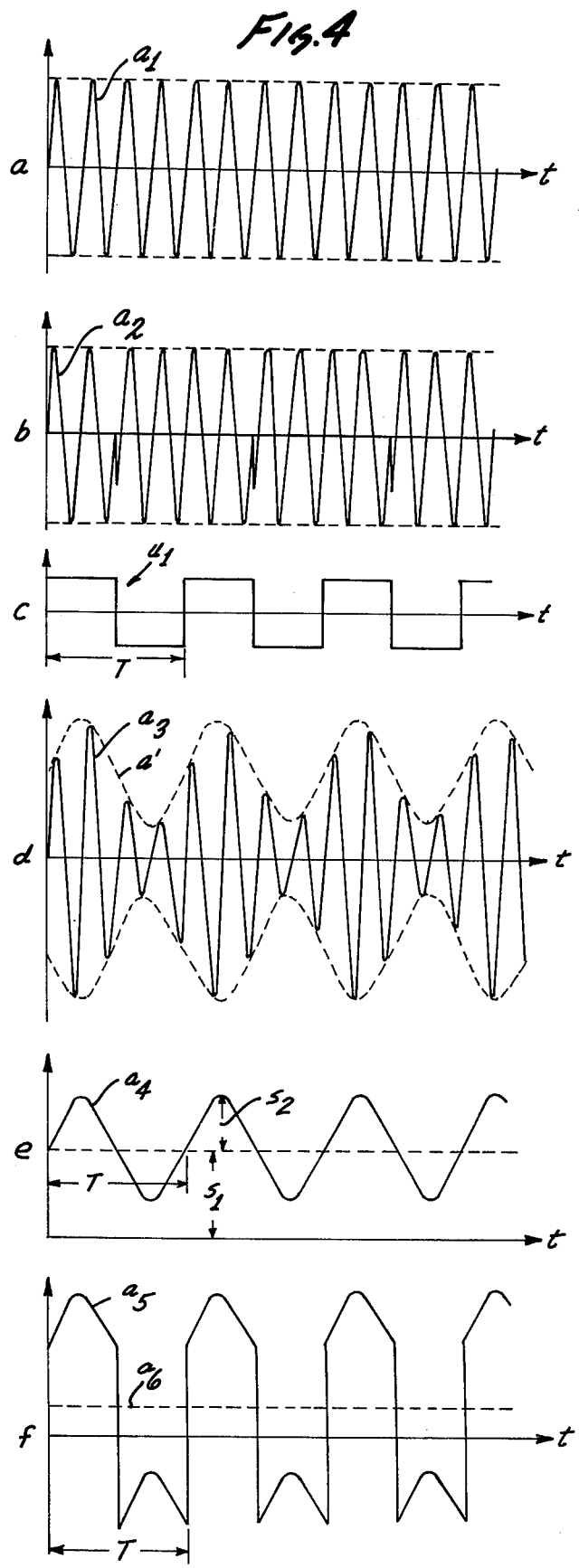

CONTROL OF MICROWAVE GENERATOR-CAVITY RESONATOR COMBINATIONS FOR GAS ANALYZER

BACKGROUND OF THE INVENTION

The present invention relates to gas analysis by means of microwaves and more particularly, the invention relates to an electric circuit for operating a cavity resonator in a microwave gas analyzer.

A gas analyzer of the type referred to above is disclosed, for example, in U.S. Pat. No. 2,792,548. The device includes a cavity resonator and a microwave generator applying microwave energy to the resonator, and the cavity of the latter receives also the gas to be analyzed. The resonator is tuned to the specific absorption frequency of the particular component to be detected, and the attenuation of the tuned frequency waves in the resonator is used as representation of the concentration of that gas component.

If the resonator of such an analyzer is not driven at exactly its resonance frequency, the power through-put in the resonator change, and any measurment is no longer adequately representative or even outright faulty. Such changes in frequency can readily occur, e.g. on account of temperature drift, mechanical vibrations, etc., unless one controls the frequency output of the microwave generator to track the changing resonance frequency in the cavity.

High performance analyzers for high sensitivity of measurement are correspondingly very sensitive to any change or difference between generator and resonator frequencies. Such differences are already noticeable even if considersably smaller than the band width of the abosrption line of interest. Thus, the frequency deviation must remain well below that band width.

The known circuits for frequency control of a microwave generator and cavity resonator are usually provided with a particular microwave circuit which extracts signals from the resonator and the microwave generator and furnishes a voltage (error signal) repesenting the difference in frequencies. This voltage is amplified and controls the frequency determining element in the generator in a typical closed loop, feedback configuration (see e.g. "Frequency Stabilisation of Microwave Oscillators", R. V. Pound Proc. I.R.E., Vol. 35, pages 1405 to 1415, December 1947). It is inherent that such a control system is rather expensive on account of the need for detecting actual frequencies as they occur or are effective and which are in the microwave range.

DESCRIPTION OF THE INVENTION

It is an object of the present invention to provide a new and improved circuit and control system for a microwave generator which permits ready tracking of a resonator frequency, the resonator being connected to the generator and serves as measuring chamber for gas analysis.

In accordance with the preferred embodiment of the present invention, it is suggested to provide a cavity resonator of the reflector variety and to control the frequency furnished to it by a microwave generator as follows. The signal of the latter is subjected to phase modulation by synchronous switching prior to passage to the resonator. A reflected component thereof is coupled out of the resonator and subjected to detection-demodulation to extract from the coupled out signal a variable component being indicative of a deviation in frequency between the microwave generator and the resonator, and an invariable component of that extracted signal represents the measured concentration of gas fed to (or through) the resonator. The variable component is then used to control the frequency of the microwave generator. The modulation and demodulation is carried out in synchronism with each other under utilization of a pulse source, e.g. a square wave signal. The demodulation includes additionally rectification and low pass filtering. The phase modulation includes particular phase shifting coupled with amplitude modulation of the shifted signal to obtain a definite vector being added or not in alternating sequence to the signal furnished by the microwave generator.

The invention is based on the discovery that the resonator should not receive a monochromatic signal, but a signal with definite side bands, i.e. a particular spectrum, so that the envelope of the reflected component has an amplitude which directly represents the deviation between resonator and microwave generator frequencies. Thus, that deviation does not have to be generated separately, but the variable, coupled-out component yields directly a representation of the location of the center frequency of the fed-in spectrum relative to the resonator frequency.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is a block diagram of the phase modulator used in the system of FIG. 1;

FIGS. 4a through f are signal diagrams for signals as they appear at various points in the system shown in FIGS. 1 and 2.

Proceeding now to the detailed description of the drawings, FIG. 1 shows a microwave generator 1 of known construction which provides the raw signal to a phase modulator 3, being controlled by a square wave generator 2. The generator 1 is deemed to be tuned to the center frequency of the narrow absorption band of a gas component. The output of the phase modulator 3 is a spectrum signal which has a very narrow banded center frequency and definitely located side bands, depending on the amount of phase shifting and on the rate of alternation between the original and the phase shifted signal as so provided by device 3.

Figure 1:
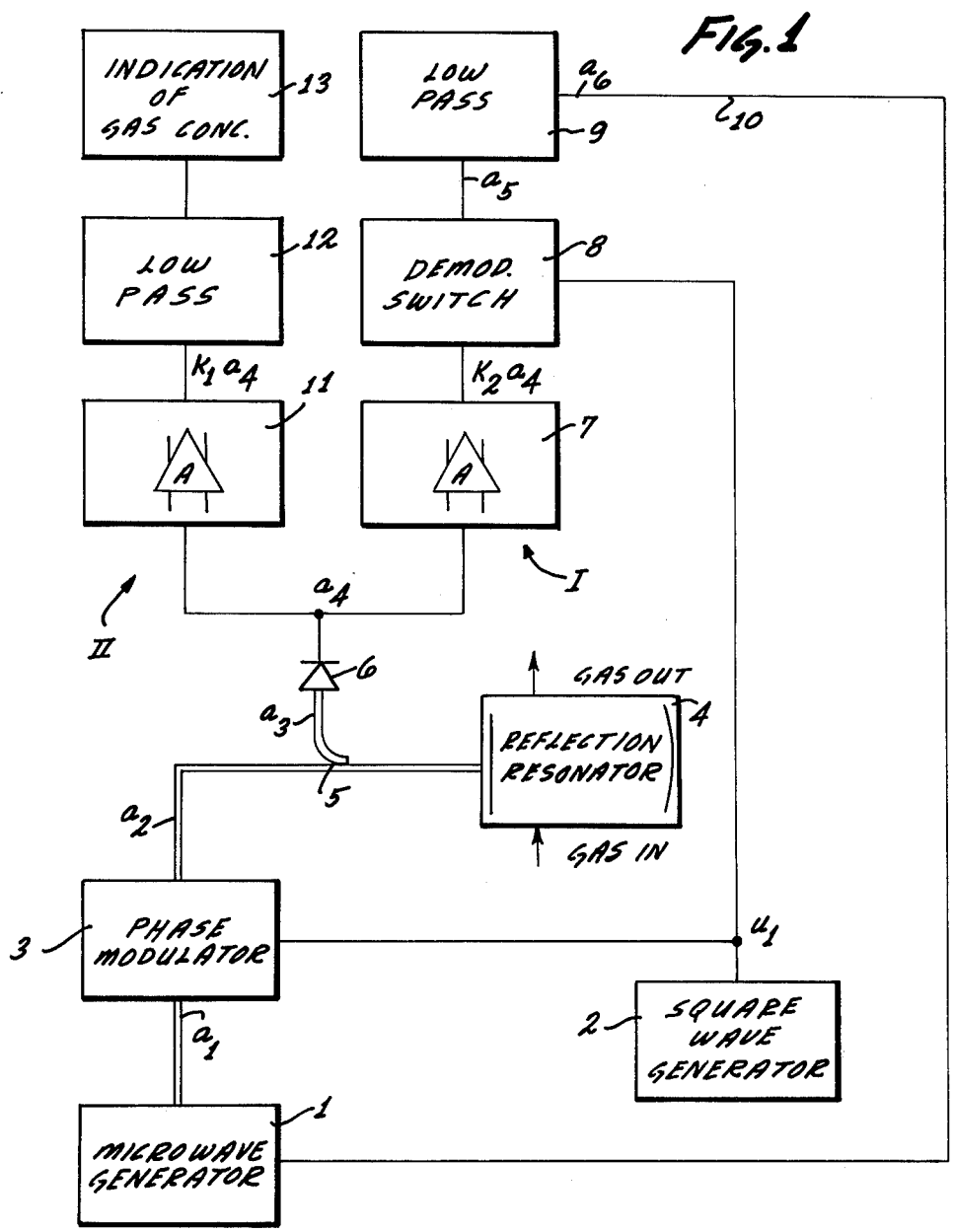
FIG. 1 is a block diagram of a control system in accordance with the preferred embodiment.

The output of modulator 3 is coupled to a cavity resonator 4 which is also supplied with gas containing the particular absorbing component to be detected. The resonator 4 is of the reflection variety and has been tuned to the frequency provided by the microwave generator being also the center frequency of the spectrum signal from modulator 3.

A directional coupler 5 is responsive to the return wave coupled out of the resonator, and that wave component ($a_3$, FIG. 4a) as tapped, is rectified at 6 to obtain a particular signal ($a_4$, FIG. 4e). That signal is passed into two channels, I and II, to separate two distinct components from each other.

Considering first channel I, it includes an amplifier 7 whose output is passed through a periodically operated switch 8. That switch is in particular driven by the square wave generator 2 to establish a synchronous demodulation. This channel extracts from the coupled out and rectified signal a component which is actually indicative of a deviation between the center frequency of the fed-in spectrum and the actual, current, resonance frequency of resonator 4. The output signal of switch 8 is fed through a low pass filter 9 which forms an average (in time) value of the signal passing switch 8.

Line 10 indicates the control connection from the low pass filter 9 to the generator 1, so as to obtain a closed loop for controlling the generator output frequency for tracking the resonator frequency of the cavity resonator. Generator 1 has a known element which determines its frequency and line 10 feeds a control signal to the immediate control circuit for that frequency determining component in generator 1. The immediate frequency control of such a generator is known and does not require elaboration. The signal in line 10 is at that point quite equivalent to an error signal even though it has been formed differently, i.e. without extracting signals from devices 1 and 4 which represent the relevant frequencies and comparing them separately.

Channel II includes also an amplifier, 11, having a gain $K_1$, and its output is fed through a low pass filter 12 to a display or recording instrument 13, being calibrated to indicate the concentration of the component of interest in the gas passed through resonator 4. This channel, thus, extracts from a component the signal derived from the resonator, which component is indicative of the particular gas concentration in the resonator cavity.

The phase modulator (FIG. 2) is constructed as follows. The input signal $a_1$ from generator 1 (FIG. 4a) is divided and passed into two channels III and IV. Channel III leads straight through to the output of the modulator. Channel IV extends parallel to channel III and merges with the latter at the output of the modulator. The channel IV is alternatingly opened and blocked so that the output signal of the modulator alternates between the unaffected input signal, and the input signal to which the channel IV adds a phase shifted and amplitude modified component.

In particular, channel IV includes an attenuator 14 for reducing the signal $a_1$, and the attenuated signal is passed to a phase shifter 16, which, in turn, provides a phase shifted signal to a diode switch 16, which is controlled from the square wave generator 2. Switch 16, thus, alternates between blocking and passing of the attenuated, phase shifted signal. The two signal components from channels III and IV are then combined to form the common output signal $a_2$.

Figure 3:
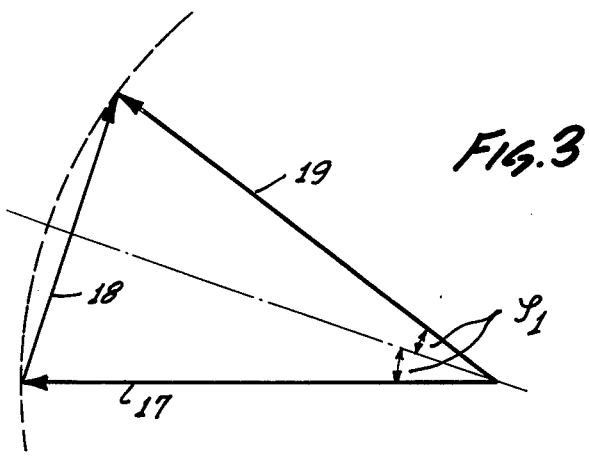
FIG. 3 is a vector diagram for demonstrating certain operational aspects of the phase modulation shown in FIG. 2.

FIG. 3 illustrates the vector diagram of the output signal of modulator 3. Whenever diode 16 blocks the channel IV, the output signal $a_2$ is identical with the input signal $a_1$ denoted by vector 17. Whenever diode 16 opens signal passage through channel IV, the vector 18 is added to vector 17 and the output signal is, for example, represented by vector 19. The phase shift angles $\phi_1$ can be varied over a wide range, by phase and amplitude variations of the signal in channel IV. Since diode 16 serves only as a switch, the modulator is independent from small amplitude variations of the modulator voltage. Moreover, the added component 18 should have an amplitude so that vectors 17 and 19 are at least approximately of equal length.

FIG. 4b shows representatively the signal $a_2$, for an input signal $a_1$ shown in FIG. 4a, while the diode switching, modulator signal is the pulse train $u_1$ plotted in FIG. 4c. One can readily see the phase jump at each of the signal flanks of $u_1$. More generally, the modulated signal $a_2$ can be identified by $$a_2 = \begin{cases} a_o \sin(2\pi f_o t + \phi_1) \text{ for } nT < t < (2n+1)\frac{T}{2} \\ a_o \sin(2\pi f_o t - _1) \text{ for } (2n+1)\frac{T}{2} < t < (n+1)T \end{cases}$$

wherein $n$ is an integer, $T$ is the oscillating period of the modulator signal $u_1$ provided by the generator 2, $f_o$ is the microwave generator frequency, $a_o$ the amplitude of the output signal of the demodulator and $\phi_1$ is the phase angle as shown in FIG. 3.

A Fourier analysis of the signal $a_2$ yields a frequency spectrum which is comprised of a resonance line or center frequency and discrete side bands constituted by lines of declining intensity. That is the signal being fed into the resonator cavity; it is not a monochromatic signal.

FIG. 4d represents the signal coupled out of the cavity by coupler 5. If resonator and microwave generator frequencies are not identical, this signal waxes and vanes along an envelope $a^1$. The frequency of this modulation component is equal to the modulator signal frequency corresponding to the period T. The rectifier 6 produces a d.c. signal $a_4$ of variable amplitude. This signal has, therefore, two components. The first component is the true or average d.c. level $S_1$ which is directly repesentative of the gas concentration to be measured, provided, however, cavity resonator and microwave generator frequencies are identical.

The oscillatory component superimposed upon level $S_1$ has an amplitude $S_2$ which represents the deviation of the frequencies. The frequency of the oscillatory component is, of course, equal to the pulse train frequency from generator 2.

The signal $S_1$ is, in fact, the component signal being indicated at 13 because low pass 12 eliminates the oscillatory component from signal $a_4$. The signal $a_4$, as processed in channel I, is subjected to the switching action of switch 8. As stated, switch 8 as controlled from pulse source 2 provides for a synchronous demodulation to extract the amplitude $S_2$ as a d.c. signal from the coupled-out and rectified resonator signal. The output signal of demodulator switch 8 is the signal $a_5$, plotted in FIG. 4f. This particular signal can be analytically represented as $$a_5 = \begin{cases} + k_2 a_4 \text{ for } nT < t < (2n+1)\frac{T}{2} \\ - k_2 a_4 \text{ for } (2n+1)\frac{T}{2} < t < (n+1)T \end{cases}$$

wherein $n$ is again an integer, $K_2$ is the gain of amplifier 7 in channel I. The low pass 9 eliminates the oscillatory component from that signal and provides an output signal at level $a_6$ which is, in fact, proportional to $S_2$. As was stated above that signal is passed through line 10 to the microwave generator 1 to serve therein as frequency control signal. Thus, the feedback loop operates to reduce $S_2$ and $a_6$ to zero. The operation of switch 8 actually furnishes the output signal $a_6$ at different polarities, depending on whether the frequency deviation between resonator and generator is positive or negative. The phase relation of the switching signal $u_1$ to the oscillatory component of $a_4$ is directly related to the sign of that deviation so that the control signal $a_6$ has the proper polarity.

The resonator is near-critically coupled. The theory reveals that under such conditions the control is quite insensitive to any additional amplitude variations (of $a_1$ or $a_2$). Such amplitude modulation may occur if the attenuation 14 and phase shift 15 are slightly detuned so that the resultants 19 are no longer on a circle (with 17). The coupling determines the degree of reflection of resonator 4. Upon calibration with zero component gas present in the host gas, one can, therefore, predetermine the basic reflection within rather wide limits. Presence of an absorbing gas component increases reflection, and the measuring signal, being indicative of concentration, is then derived therefrom as outlined above.

It can, thus, be seen that the inventive system is simple as compared with circuits in which frequency dependent control signals are separately extracted from resonator and microwave generator, compared etc. The present system uses but one (instead of two) rectifier, namely rectifier 6. Also, the modulator 3 is of rather simple construction. It can be said that the resonator 4 fulfills dual functions. Its primary function is, of course, to provide particular absorption of microwave energy on the basis of the gas component and its concentration. In addition, however, it can be seen that the resonator generates the oscillatory signal $a^1$ and $S_2$, which is then used as frequency control or error signal without direct formation of such a signal by external circuitry. In other words, feeding the resonator cavity with a spectrum signal causes the resonator to generate directly the equivalent of an error signal which is then coupled out as such, and the circuit as described simply extracts that error signal and separates it from the true measuring signal also included in the coupled-out wave.

The invention is not limited to the embodiments described above but all changes and modifications thereof not constituting departures from the spirit and scope of the invention are intended to be included.

I claim:

1. In a gas analyzer which includes a microwave generator and a cavity resonator for the gas to be analyzed, the generator providing microwaves at a particular frequency, the resonator having a particular resonance frequency, the frequencies should be equal, the improvement comprising:
   means for extracting from said resonator a first signal representing an attenuation of microwaves by the gas in the resonator, and a second signal representing a difference between the resonance frequency of the resonator and the particular frequency as provided by the generator;
   means connected for feeding the second signal to the generator for causing the generator frequency to track the resonance frequency; and
   means for connecting the generator to the resonator for feeding the microwaves to the resonator to obtain therein the attenuation by the gas.

2. Analyzer as in claim 1, said means for connecting, including a phase modulator, said means for extracting the second signal including a phase demodulator.

3. Control apparatus for a microwave gas analyzer which includes a microwave generator and a cavity resonator receiving a gas having a component to be detected through absorption of microwave energy at a particular frequency to which the resonator is tuned, the generator providing microwave energy at said frequency, comprising:
   the cavity resonator being a reflection resonator;
   a phase modulator connected to the generator to receive therefrom the microwave energy, and passing microwave energy to the resonator;
   a pulse source connected for controlling the phase modulator;
   a directional coupler for extracting reflected energy from the resonator;
   a detector-demodulator connected to said coupler having a first and a second output channel, the first channel including circuit means responsive to the d.c. component of the signal as extracted by the coupler in representation of said concentration, the second channel including circuit means responsive to the variable component of said extracted signal, repesenting a difference in frequency between the frequency of the microwave generator and the frequency to which the resonator is tuned, and providing a control signal representative thereof; and
   means for feeding such control signal to said generator for controlling the frequency thereof.

4. Apparatus as in claim 1, said phase modulator including two parallel channels, one of them including an attenuator, a phase shifter and a switch, all connected in series, said switch being controlled by said pulse train, to provide a phase and amplitude modulated signal relative to the signal in the other one of the channels.

5. Apparatus as in claim 1, wherein the detector demodulator includes a rectifier, and switching means connected for operation in response to said pulse train to extract said variable component from the coupled-out signal.

6. Apparatus as in claim 1, wherein the detector-demodulator includes a rectifier, a low pass filter connected to the rectifier, and an indicator connected to the low pass filter for indicating said d.c. component.

7. In a gas analyzer which includes a microwave generator and a cavity resonator for the gas to be analyzed, the generator providing microwaves at a particular frequency, the resonator having a particular resonance frequency, the frequencies should be equal, the improvement comprising:
   means connected to said generator to extract therefrom said microwaves and generating a spectrum which includes a center frequency and particular side bands, and further connected for feeding said spectrum to said resonator;
   means for extracting from said resonator a signal with variable amplitude having frequency below the microwave frequency, the variation representing a difference between said center frequency and said resonance frequency; and
   means connected to be responsive to said variable amplitude signal for controlling the generator towards agreement of the center frequency with the resonance frequency.

8. In an analyzer as in claim 7, wherein said spectrum generating means includes a phase modulator, the resonator being of the reflector variety.

9. In an analyzer as in claim 7, wherein said first means and said third means, respectively, include synchronously operated phase modulator and demodulator.

* * * * *